United States Patent [19]
Rechmann

[11] Patent Number: 5,501,599
[45] Date of Patent: Mar. 26, 1996

[54] DEVICE FOR REMOVING CARIOUS TOOTH MATERIAL BY LASER LIGHT AND USE OF A LASER LIGHT SOURCE

[76] Inventor: Peter Rechmann, Dellestrasse 79, Duesseldorf-Unterbach, Germany

[21] Appl. No.: 292,173

[22] Filed: Aug. 19, 1994

Related U.S. Application Data

[63] Continuation of Ser. No. 946,352, filed as PCT/EP91 00831, May 3, 1991, abandoned.

[30] Foreign Application Priority Data

May 4, 1990 [DE] Germany ............... 40 14 303.1

[51] Int. Cl.$^6$ ........................................... A61C 5/00
[52] U.S. Cl. ................... 433/215; 433/216; 606/3; 606/10; 606/13
[58] Field of Search ............... 606/2, 3, 10–16; 433/215, 216

[56] References Cited

U.S. PATENT DOCUMENTS

| | | | |
|---|---|---|---|
| 4,521,194 | 6/1985 | Myers et al. | 433/215 |
| 4,784,135 | 11/1988 | Blum et al. | 606/3 |
| 4,818,230 | 4/1989 | Myers et al. | 433/215 |
| 4,940,411 | 7/1990 | Vassiliadis et al. | |
| 4,981,138 | 1/1991 | Deckelbaum et al. | 128/665 |
| 5,020,995 | 6/1991 | Levy | 438/216 |
| 5,084,043 | 1/1992 | Hertzmann et al. | 606/13 |
| 5,118,293 | 6/1992 | Levy | 433/215 |
| 5,281,141 | 7/1994 | Kowalyk | 433/215 |

FOREIGN PATENT DOCUMENTS

| | | |
|---|---|---|
| 1392614 | 2/1964 | France. |
| 2598608 | 5/1986 | France. |
| 3800555 | 1/1988 | Germany. |
| 89/01317 | 4/1988 | WIPO. |
| 90/00035 | 6/1989 | WIPO. |
| 90/01907 | 8/1989 | WIPO. |
| 9001907 | 3/1990 | WIPO. |

OTHER PUBLICATIONS

"The Laser Guidebook", pp. 38–41; 290–295, (J. Hecht, McGraw-Hillbook Comp. 1986).

*Primary Examiner*—Stephen C. Pellegrino
*Assistant Examiner*—Michael Peffley
*Attorney, Agent, or Firm*—Diller, Ramik & Wight

[57] ABSTRACT

A method of removing carious tooth material is effected by creating a laser light beam from a pulsed laser light source, and utilize a flexible light guide to direct the laser light beam as a light spot on carious tooth material of a tooth. The light source has a wavelength in the range from substantially 320 to 520 nm and the energy density per pulse in the light spot is substantially 0.14 to about 7.0 J/cm$^2$.

14 Claims, 3 Drawing Sheets

5,501,599

DEVICE FOR REMOVING CARIOUS TOOTH MATERIAL BY LASER LIGHT AND USE OF A LASER LIGHT SOURCE

This application is a continuation of application Ser. No. 07/946,352, filed as PCT/EP91/00831, May 3, 1991, now abandoned.

BACKGROUND OF THE INVENTION

The invention is directed to a device for and a method of removing carious tooth material by laser light emitted from a pulsed laser light source.

From DE 38 00 555 A, the use of ultraviolet laser light with a wavelength of 193 nm is known, which is emitted from an argon fluoride excimer laser. The photon energy of the laser light is cumulated to magnitudes that are greater than the binding energies of the respective hard tooth substances to be dissolved. With an energy density of at least 5000 mJ/mm$^2$ per pulse and focussing on a light spot of about 1–2 mm$^2$, it is said to be possible to generate a pulse energy density at which the threshold value to the beginning of photodecomposition is exceeded by a sufficient extent. For the repetition reate, it is suggested to select a frequency of less than 100 Hz. The laser pulse period is about 15 to 20 ns. This known method is to allow for a controlled removal of unaffected or carious hard tooth substances. From U.S. Pat. Nos. 4,521,194 and 4,818,230, it is known to use an yttrium aluminium garnet laser (wavelength 1064 nm), the output energy of which is within the range of 1 to 100 mJ at a pulse duration of several picoseconds to several milliseconds, and the light beam diameter of which is in the range of 50 to 2000 μm.

The known devices allow for a treatment of both carious dentine and non-carious softened dentine. Here, it is a drawback that, as in conventional drilling, unaffected hard tooth substance is removed when removing carious dentine or carious tooth material, thus leading to an unnecessary reduction of the hard tooth substance.

It is a further drawback of known prior art that a high energy density is introduced so that the thermal stress on the tooth may also cause damages to adjacent areas.

A further problem arises with laser devices that require a focussing of the laser beam: with these devices, an exact observation of a defined distance is necessary in order to keep the light spot diameter, and thus the energy density introduced, constant. To accomplish this, complex devices are required that also hinder a dentist's work.

From the posteriorly published EP 0 375 578 A, a Nd:YAG laser with a wavelength of 532 nm is known to be used for dental treatment. The output energy of the laser per pulse is 10 to 50 mJ at a frequency of 50 Hz. The pulse duration is between 100 and 300 μs. The laser beam is focussed onto a light spot diameter between 0.2 and 0.6 mm via a converging mirror.

SUMMARY OF THE INVENTION

It is the object of the invention to provide a device for removing carious tooth material with which it is possible, at minimum energy levels, to selectively and completely remove carious tooth material while providing for a maximum protection of the unaffected hard tooth substance, as well as to explain the use of special laser parameters for this purpose.

In order to solve this object, it is provided according to the invention that in a device for removing carious tooth material with a laser light beam generated by a pulsed laser light source and a flexible laser light guide through which the laser light beam produces a light spot on a tooth to be treated, the laser light source emits laser light with a wavelength in the range between 320 and 520 nm and that, per laser light pulse, the pulsed laser light has an energy density in the light spot of about 0.14 to about 7.0 J/cm$^2$.

The use of a wavelength in the range from 320 to 520 nm allows for a selective removal of carious substance, since in this spectral range carious tooth material absorbs laser light to a greater extent than unaffected dentine.

The ablation thresholds for carious tooth material and unaffected dentine show the greatest difference in this range so that the comparatively softer carious tooth material may be removed selectively due to a reduceable energy density at minimum thermal stress.

Preferably, the laser light guide may be directed onto the tooth to be treated either in the contact mode or at a distance of a few millimeters. Since a focussing is not required, the laser beam may be applied to the spot to be treated in the contact mode, whereby an exact working is possible and complex spacers are superfluous. Moreover, one may also operate from a distance to the ablation site. An essential advantage hereof is that despite distance variations of a few millimeters, energy densities above the ablation threshold of carious dentine are obtained.

Preferably, an energy density per laser light pulse is used that lies within the range from 0.175 to 2.0 J/cm$^2$. A preferred wavelength is about 355 nm to 375 nm. In the range of this wavelength, there is a maximum absorption difference between unaffected dentine and carious tooth material so that an optimum selection between dentine and carious tooth material may be obtained with lower energy density. If the wavelength of the laser light varies from the optimum wavelength, one may use an energy density correction factor K that depends on the wavelength λ. With this corrected energy density, one will still obtain a satisfactory selection in which only carious dentine and practically no unaffected dentine is removed, even when the wavelengths differ from the optimum.

The use of a laser for removing hard tooth substance, dentine and carious dentine is characterised, according to the present invention, by the selective ablation of a wavelength of about 350–410 nm, preferably about 375 nm, and an energy density in the light spot per laser light pulse in the range from 0.35 to 1.7 J/m$^2$.

At a pulse duration of more than 50 ns, the energy is preferably increased by a factor F that is proportional to the root of the ratio of the set pulse duration and a basic pulse duration of 10 ns. Accordingly, the following relation is true for F at a pulse duration I:

$$F \sim \sqrt{\frac{I[s]}{10^{-8}[s]}}$$

The factor takes the effect of thermal diffusion into account that occurs from about 50 ns onward.

One embodiment contemplates the use of a repetition frequency below 12 Hz. At frequencies below 12 Hz, an additional cooling may be dispensed with.

In another embodiment, a repetition frequency between 100 and 200 Hz is preferred.

Preferably, a frequency-doubled alexandrite laser is used.

The following is a detailed description of an embodiment of the invention taken in conjunction with the accompanying drawings. In the Figures:

BRIEF DESCRIPTION OF THE DRAWINGS

FIG. 1 shows the transmission spectrums of carious dentine (solid line), unaffected dentine that is not softened by carious tooth material (chain line), and enamel (dotted line).

DESCRIPTION OF THE PREFERRED EMBODIMENTS

The ordinate represents the extinction and the abscissa represents the wavelength of the light.

The transmission spectrums show that, in the illustrated wavelength range between 240 and 770 nm, carious dentine absorbs laser light to a much greater extent than dentine not softened by carious tooth material. In the wavelength range between 250 and 320 nm, both transmission spectrums show the charactersitic UV-absorption properties of aromatic amino acids and nucleic acids with maximum absorptions of about 280 nm. Enamel is composed of 96–98 % of anorganic components and thus has no substantial absorption band.

In the range of longer waves above 320 nm, proteines have no real absorption, if they are not in conjugation with a coenzyme or a prosthetic group.

Figure 1:
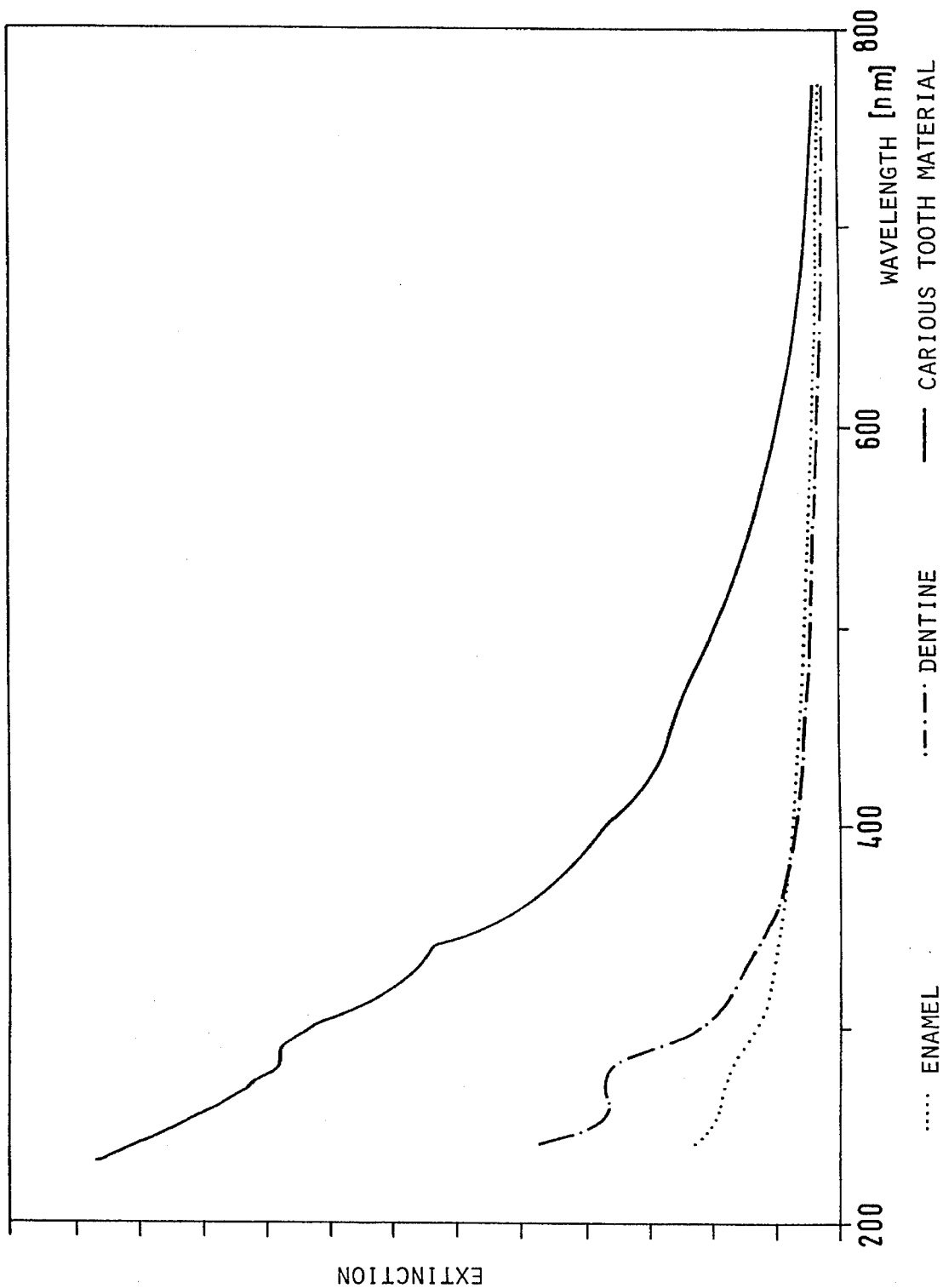
FIG. 1 illustrates the transmission spectrum of carious and unaffected dentine not softened by carious tooth material, as well as of enamel.
Figure 2:
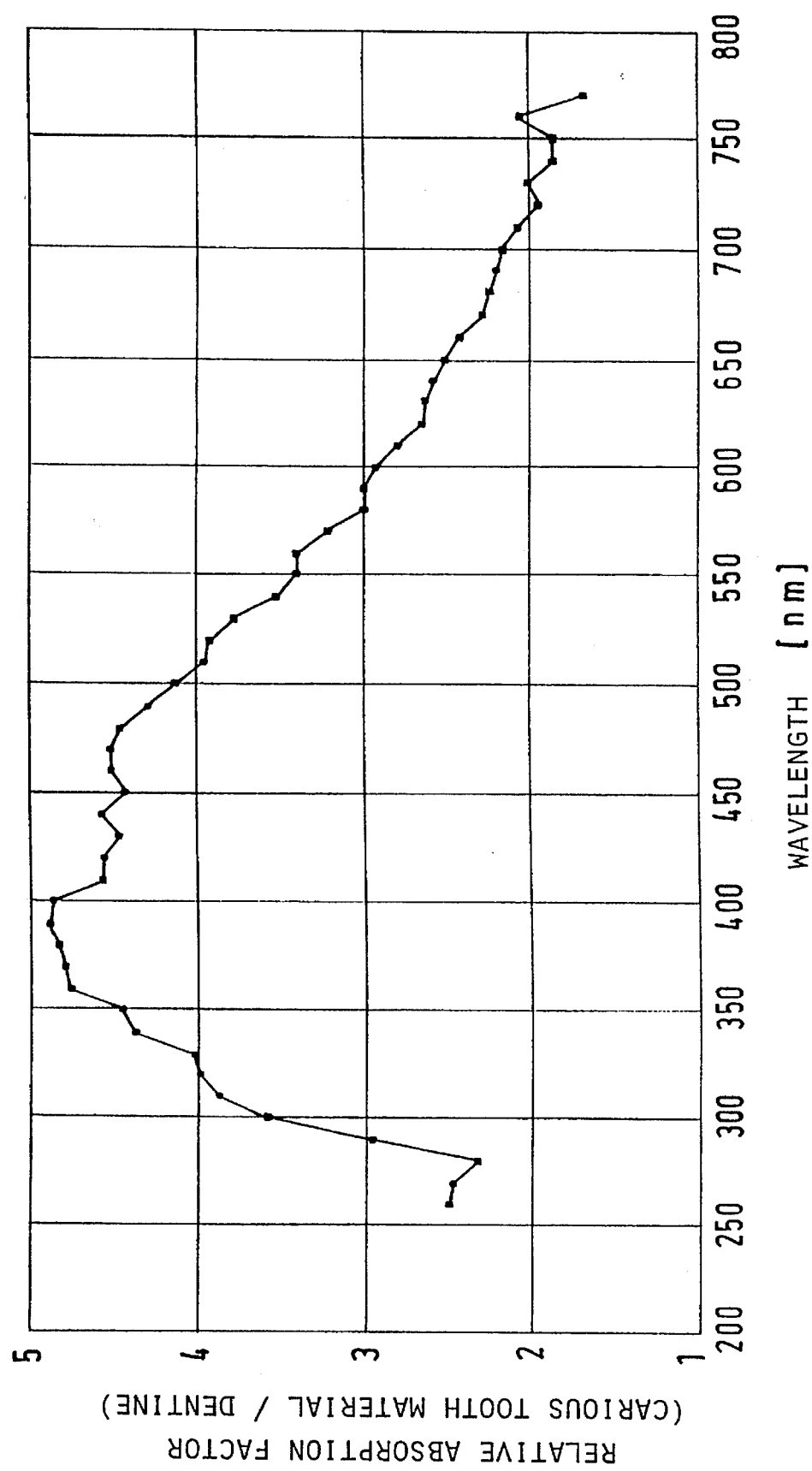
FIG. 2 illustrates the absorption factor of carious tooth material to dentine as a function of the wavelength of the laser light.

In FIG. 2, the abscissa represents the wavelength of the irradiated light. The ordinate presents the optical density of carious tooth material relative to the optical density of dentine. Here, the value 1 means that there is a difference between the optical density of carious tooth material and dentine not softened by carious tooth material.

In the spectral range from 320 to 520 nm, the largest relative absorption differences exist. Dentine softened by carious tooth material absorbs 4–5 times more than dentine not softened by carious tooth material.

The use of a wavelength in the range between 300 and 700 nm, preferably between 320 and 520 nm, allows for a selective removal of carious substance.

For a selective removal of dentine softened by carious tooth material, the irradiated energy density must be below the ablation threshold of dentine not affected by carious tooth material.

In order to remove carious tooth material, the energy density of the laser pulse must be varied in dependence on the wavelength used. As the wavelength of the laser light increases, the ablation thresholds of dentine and cavities increase in about the same extent. The relationship between the threshold values for an ablation of dentine cavities or dentine, however, remain substantially the same above the preferred wavelength ranges between 320 and 520 nm.

Figure 3:
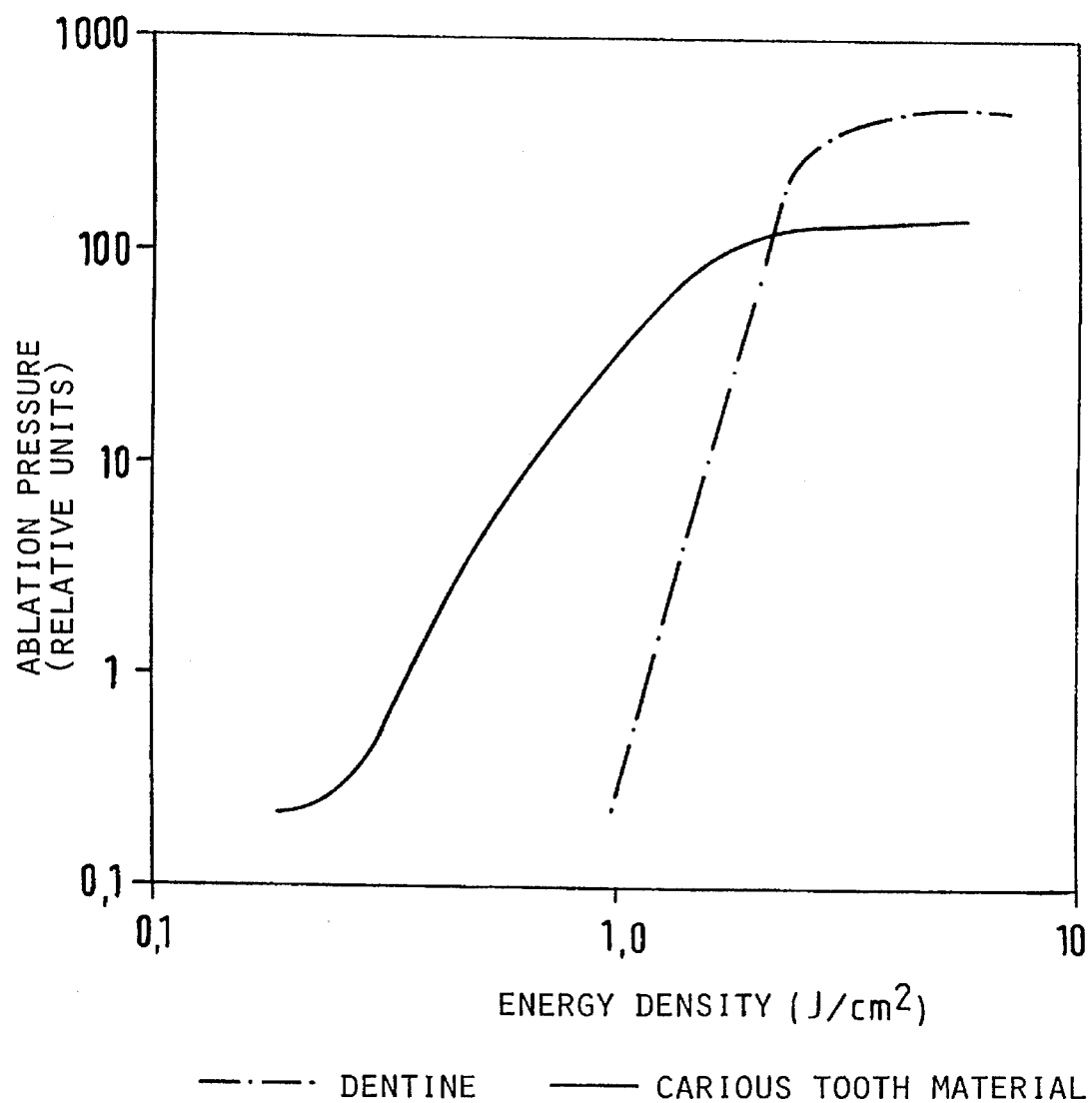
FIG. 3 illustrates the ablation pressure of dentine and carious tooth material as a function of the energy density.

As a light source for detecting the relationship according to FIG. 3, a frequency-tripled and Q-switched Nd:YAG laser has been used that emits laser light with a wavelength of 355 nm and a light pulse duration of 9 ns.

FIG. 3 illustrates the dependence of the ablation pressure on the energy density of the laser light for carious dentine (solid line) and dentine not softened by cavities (chain line) at a pulse duration of 9 ns for the laser used in the embodiment. The graph for dentine not softened by carious tooth material is shifted towards higher energy densities. The energy threshold value for the ablation of carious tooth material is at a value of about 0.35 J/cm$^2$ at a pulse duration of 9 ns. In contrast thereto, the threshold value for unaffected dentine is above an energy density of 1.0 J/cm$^2$. Thus, there is a relationship of about 3:1 between the ablation thresholds of carious tooth material and dentine not softened by carious tooth material.

Operating with energy densities between about 0.35 and 1.0 J/cm$^2$ at a wavelength of about 355 nm to 375 nm, carious tooth material is selectively removed. The non-carious dentine is not disturbed (FIG. 3).

In a preferred embodiment with a wavelength of 375 nm, the energy density is 1.3 J/cm$^2$.

For the wavelength range of 355 nm, an optical density of about 1.0 has been found (table). If laser light with a wavelength of, e.g., 520 nm is to be used, one may take the optical density value of about 0.3 from the table.

This means that only about one third of the irradiated energy is absorbed compared to the wavelength of 355 nm. Thus, the ablation thresholds shift by the factor 3 towards higher values. Yet, the selectivity for the removal of dentine softened by carious tooth material is preserved. At this wavelength (520 nm), the energy densities for a selective removal of carious tooth material are between 1.2 and 3.3 J/cm$^2$.

The table presents a factor for each wavelength in the preferred range between 320 and 520 nm, with which the required energy density for a selective removal of carious tooth material may be calculated. By multiplying the energy density range in which a selective ablation occurs at 355 nm (0.35 to 1.0 J/cm$^2$) with the corresponding factor K of the desired wavelength, the required energy density for a selective removal of carious tooth material at this wavelength will be obtained.

In the range between 330 and 480 nm, the energy density correction factor K may be calculated from $$K=0.0115 \ nm^{-1} \cdot \lambda - 3,$$

deviations of ±10% of the correction factor being possible due to inaccuracies of measurement.

TABLE

| Wavelength in nm | energy density correction factor K |
|---|---|
| 320 | 0.8 |
| 330 | 0.8 |
| 340 | 0.9 |
| 350 | 1.0 |
| 360 | 1.1 |
| 370 | 1.2 |
| 380 | 1.3 |
| 390 | 1.4 |
| 400 | 1.5 |
| 410 | 1.7 |
| 420 | 1.8 |
| 430 | 1.9 |
| 440 | 2.0 |
| 450 | 2.1 |
| 460 | 2.2 |
| 470 | 2.4 |
| 480 | 2.5 |
| 490 | 2.7 |
| 500 | 2.9 |
| 510 | 3.1 |

TABLE-continued

| Wavelength in nm | energy density correction factor K |
|---|---|
| 520 | 3.3 |

The measuring accuracy of the absolute values of the energy densities is limited by the inaccuracies of the technical measuring possibilities. The limitations stem from the measuring accuracy of the energy meter, the determination of the area irradiated, as well as from inhomogeneities within the beam profile of the laser.

If need be, the pulse duration of the laser light may be varied. However, it should not exceed 10 µs or otherwise thermal damages to the adjacent tissue cannot be excluded.

At a pulse duration of the laser light above 50 ns, an increase factor F for the energy density should be used, preferably, which is proportional to the root of the ratio of the set pulse duration and a basic pulse duration of 10 ns. Preferably, the proportionality factor is 1.

The light energy densities required for the selective ablation of carious tooth material may be guided by light guides, the diameters of which may be adapted to the dimensions of the carious lesion; it is possible to integrate the light guides in dentist's angle pieces. Therefore, the construction of complex application instruments is no longer necessary. The ablation of carious tooth material may be performed both in the contact mode and at a distance of several millimeters.

It is feasible to provide a visible pilot beam colinear with the invisible laser beam.

Although a preferred embodiment of the invention has been specifically illustrated and described herein, it is to be understood that minor variations may be made in the apparatus without departing from the spirit and scope of the invention, as defined the appended claims.

I claim:

1. A method of selectively removing only carious tooth material from a tooth comprising the steps of creating a laser light beam from pulsed laser light in the form of a light spot, conducting the pulsed laser light through a flexible light guide to thereby create a light spot upon a tooth, manipulating the flexible light guide to direct a light spot on carious tooth material of the tooth, maintaining the wavelength of the laser light beam in the range of substantially 320 to 520 nm, and maintaining the energy density per pulse of the light spot substantially in the range of 0.30 to about 7.0 $J/cm^2$ whereby healthy dentine and enamel are unaffected.

2. The method as defined in claim 1 wherein the energy density in the wavelength range between 330 nm and 480 nm is corrected in dependence upon the wavelength $\lambda$ by the correction factor $K=0.0115$ $nm^{-1}$ $\lambda-3$.

3. The method as defined in claim 1 wherein the pulse duration of the laser light source is less than about 10 µs.

4. The method as defined in claim 1 wherein the pulse duration of the laser light source is between 50 ns and 5 µs.

5. The method as defined in claim 1 wherein the pulse duration of the laser light source is about 9 ns.

6. The method as defined in claim 1 wherein at a pulse duration of more than about 50 ns, the energy density is increased by a factor F that is proportional to the root of the ratio of the set pulse duration and a pulse duration of 10 ns.

7. The method as defined in claim 1 wherein the repetition frequency of said laser light source pulses is about 12 Hz at most.

8. The method as defined in claim 1 wherein the repetition frequency of said laser light source pulses is about 100 to 200 Hz.

9. The method as defined in claim 1 wherein the laser light is directed contiguous the tooth to be treated.

10. The method as defined in claim 1 wherein the pulsed laser light has an energy density per pulse in the light spot of about substantially between 0.175 to about 2.0 $J/cm^2$.

11. The method as defined in claim 1 wherein the pulsed laser light has a wavelength in the range between 350 nm and 410 nm with an energy density per laser light pulse in the light spot in the range substantially between 0.35 and 1.7 $J/cm^2$.

12. The method as defined in claim 1 wherein the wavelength of the pulsed laser light is about 355 nm to 375 nm.

13. The method as defined in claim 1 wherein the pulsed laser light has an energy density per pulse in the light spot of substantially between 0.35 to about 1.0 $J/cm^2$.

14. The method as defined in claim 1 wherein at a wavelength of about 375 nm the energy density is about 1.3 $J/cm^2$.

* * * * *